United States Patent
Schulman et al.

(10) Patent No.: US 8,055,336 B1
(45) Date of Patent: Nov. 8, 2011

(54) METHOD FOR REMOVING SURGICALLY IMPLANTED DEVICES

(75) Inventors: Joseph H. Schulman, Santa Clarita, CA (US); Yitzhak Zilberman, Santa Clarita, CA (US); Kate E. Purnell, Valencia, CA (US); Martin J. Vogel, Valencia, CA (US); Adam Vogel, legal representative, Valencia, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 1061 days.

(21) Appl. No.: 11/871,776

(22) Filed: Oct. 12, 2007
(Under 37 CFR 1.47)

Related U.S. Application Data

(63) Continuation-in-part of application No. 10/116,380, filed on Apr. 4, 2002, now abandoned.

(60) Provisional application No. 60/330,165, filed on Oct. 19, 2001.

(51) Int. Cl.
*A61N 1/05* (2006.01)
(52) U.S. Cl. .......................................................... 607/2
(58) Field of Classification Search ................ 607/2, 48, 607/116
See application file for complete search history.

(56) References Cited

U.S. PATENT DOCUMENTS

2007/0154524 A1 * 7/2007 Kauper et al. ................. 424/427
* cited by examiner

*Primary Examiner* — Carl H Layno
*Assistant Examiner* — Frances Oropeza
(74) *Attorney, Agent, or Firm* — Gary D. Schnittgrund

(57) ABSTRACT

A method of removing an implantable electronic microdevice by an integral removal loop or circumferential ring to facilitate removal of the implanted microdevice without additional surgery. The device is removed by pulling it along the surgically created implantation path. Optionally a radio-opaque tether provides a method of locating the implantable microdevice without additional surgery and attachment of one end of the tether to a radio-opaque marker provides a method of locating the end of the tether to facilitate removal of the implantable microdevice from living tissue.

2 Claims, 4 Drawing Sheets

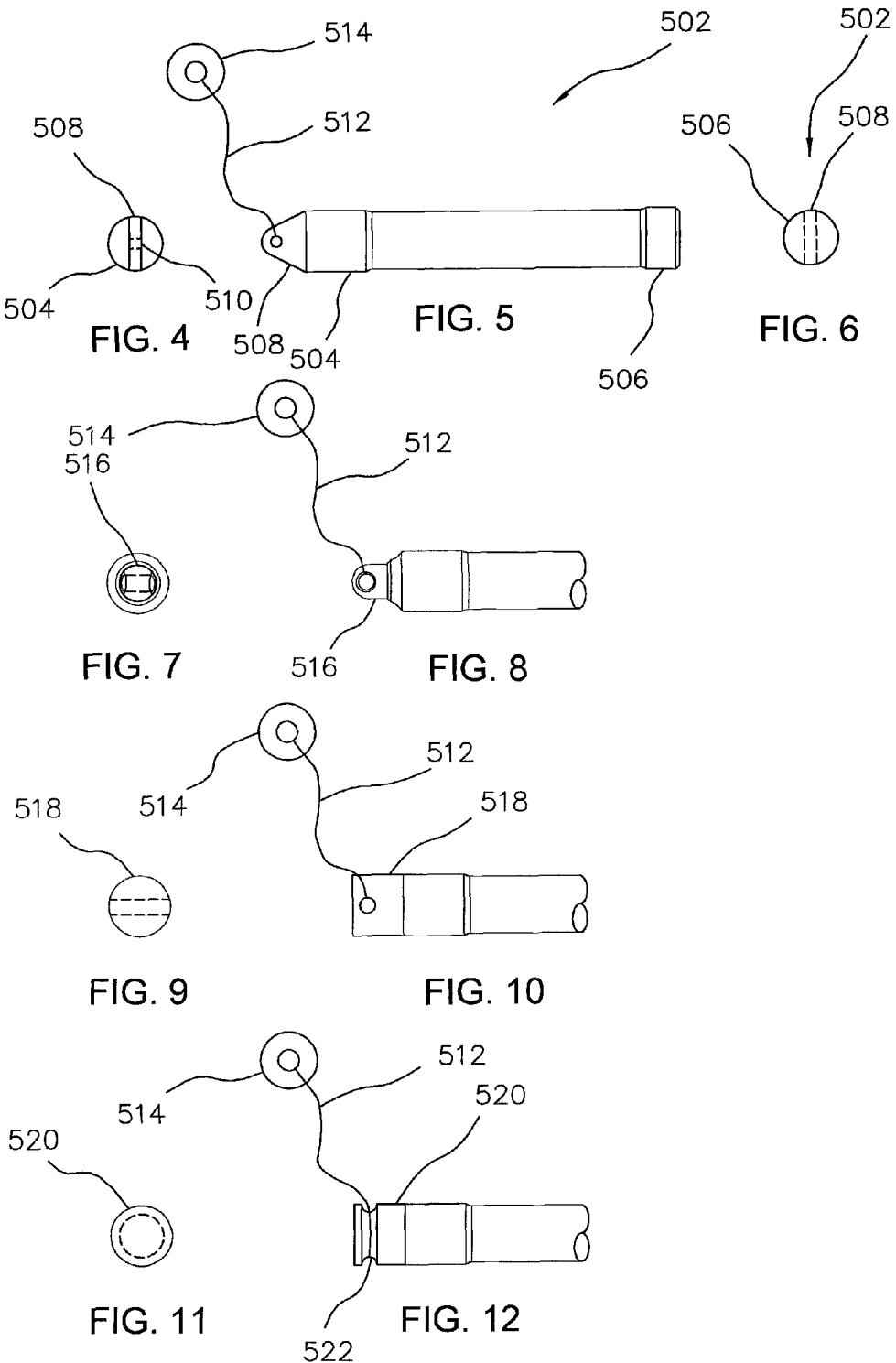

METHOD FOR REMOVING SURGICALLY IMPLANTED DEVICES

CROSS REFERENCE TO RELATED APPLICATION

Claims 1-24 are fully supported by the subject matter disclosed in the manner provided by the first paragraph of 35 USC 112 in application Ser. No. 10/116,380 filed on Apr. 4, 2002, now abandoned. This application is a continuation-in-part of U.S. patent application Ser. No. 10/116,380, filed Apr. 4, 2002, now abandoned; which claims the benefit of commonly assigned U.S. Provisional application No. 60/330,165, filed Oct. 19, 2001. This application is related to but in no way dependent on commonly assigned U.S. patent application, Electrically Sensing and Stimulating System for Placement of a Nerve Stimulator or to Sensor, incorporated herein by reference, now U.S. Pat. No. 6,829,508 B2 issued Dec. 7, 2004.

BACKGROUND OF THE INVENTION

Microstimulators are small, surgically implantable electrical microdevices that pass a small electrical signal to living tissue in order to elicit a response from a nerve or muscle. Microsensors are similar electrical microdevices except that they detect electrical and other signals that are generated by living tissue. The term microstimulator is intended to apply equally to both microstimulators and microsensors. The use of microstimulators or microsensors which are implanted in living tissue to stimulate a muscle function by either stimulating a nerve or the muscle itself are well known. The microstimulators receive power and control signals by inductive coupling of magnetic fields generated by an extracorporeal antenna rather than requiring any electrical leads. See for example, U.S. Pat. Nos. 5,193,539; 5,193,540; 5,324,316; 5,405,367; 6,175,764; 6,181,965; 6,185,452; 6,185,455; 6,208,894; 6,214,032; and 6,315,721, each of which is incorporated in its entirety by reference herein. These microstimulators are particularly advantageous because they can be manufactured inexpensively and can be implanted by minimally invasive injection. Additionally, each implanted microstimulator can be commanded, at will, to produce a well-localized electrical current pulse of a prescribed magnitude, duration and/or repetition rate sufficient to cause a smoothly graded contraction of the muscle in which the microstimulator is implanted.

Microdevices, as exemplified by the BION® of Advanced Bionics Corporation, are typically elongated devices with metallic electrodes at each end that deliver electrical current to the immediately surrounding living tissues. The electronic circuitry and inductive coils that control the electrical current applied to the electrodes are protected from the body fluids by a hermetically sealed capsule. This capsule is typically made of a rigid dielectric material, such as glass or ceramic, which transmits magnetic fields but is impermeable to water.

Often, while placing the miniature microstimulator in living tissue, the orientation of the microstimulator changes slightly such that the microstimulator is not in fact in electrical contact with the nerve, requiring reorientation of the microstimulator. The microstimulator may move at any point in the surgical implantation procedure. If the microstimulator has moved, it may be at a significant distance from the nerve that is to be stimulated. Consequently, more energy is needed from the microstimulator to stimulate the nerve, unless the microstimulator is repositioned closer to the nerve. While such microstimulators may be injected, the actual placement requires first locating the desired end point at a nerve or in a muscle. The method of placement involves locating the nerve with an electric probe, placing a hollow implantation tool over the electric probe and removing the electric probe to allow the microstimulator to be passed down the length of the hollow implantation tool. The implantation tool is then removed, leaving the microstimulator implanted at or near the desired location. If there is a problem with the function or location of the microstimulator, then additional surgery must be performed to remove or relocate the microstimulator, imposing risk, discomfort and potential tissue damage to the patient.

Therefore, it is desired to have a method of implantation that allows removal of the microstimulator post-implantation to allow it to be surgically re-implanted with minimal tissue disruption during its removal.

BRIEF DESCRIPTION OF THE DRAWINGS

FIG. 4 illustrates a proximal end view of the miniature implantable microdevice having a removal loop.

FIG. 5 depicts a side view of the miniature implantable microdevice having a removal loop on one end of the microdevice.

FIG. 6 depicts a distal end view of the miniature implantable microdevice of FIG. 5.

FIG. 7 depicts an end view of the miniature implantable microdevice having a removal loop.

FIG. 8 depicts a side view of the miniature implantable microdevice is having a removal loop on one end of the microdevice.

FIG. 9 depicts an end view of the miniature implantable microdevice having a removal loop.

FIG. 10 depicts a side view of the miniature implantable microdevice having a removal loop on one end.

FIG. 11 depicts an end view of the miniature implantable microdevice having a removal loop.

FIG. 12 depicts a side view of the miniature implantable microdevice having a removal loop on one end.

DETAILED DESCRIPTION OF THE PREFERRED EMBODIMENT

A microstimulator 22 (see FIG. 2) is represented by a small tubular device that contains an electronic package and communication means for modifying or affecting a body parameter when it is located near a nerve 6 or muscle to be stimulated. The nerve 6 is a specific targeted beneficial nerve that is selected because it controls a specific desired muscular function. In a preferred embodiment, the microstimulator 22 has microstimulator electrodes 23 located on each end.

Figure 1:
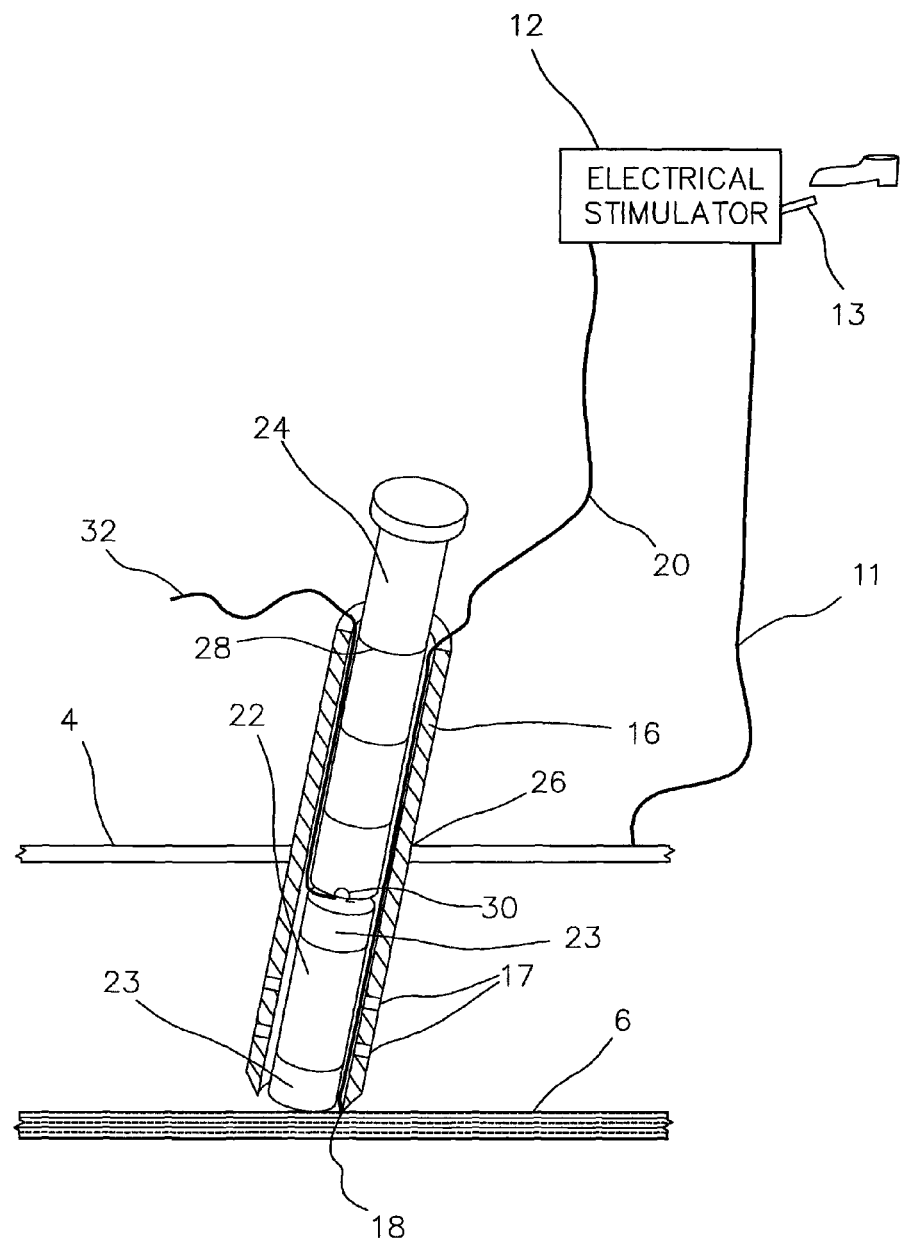
FIG. 1 depicts an outer sheath and sheath electrode at a nerve with a microstimulator being inserted by a blunt-end push rod.

FIG. 1 illustrates the microstimulator 22 being inserted into the outer sheath 16 using the blunt-end push rod 24. Alternately, the microstimulator can be inserted into the outer sheath 16 by using the electrode probe 2 or inner sheath 8. The blunt-end push rod 24 has a location mark 28 that circumscribes the push rod 24 such that the location of the microstimulator 22 in the outer sheath 16 can be ascertained by reference to the location mark 28.

Figure 2:
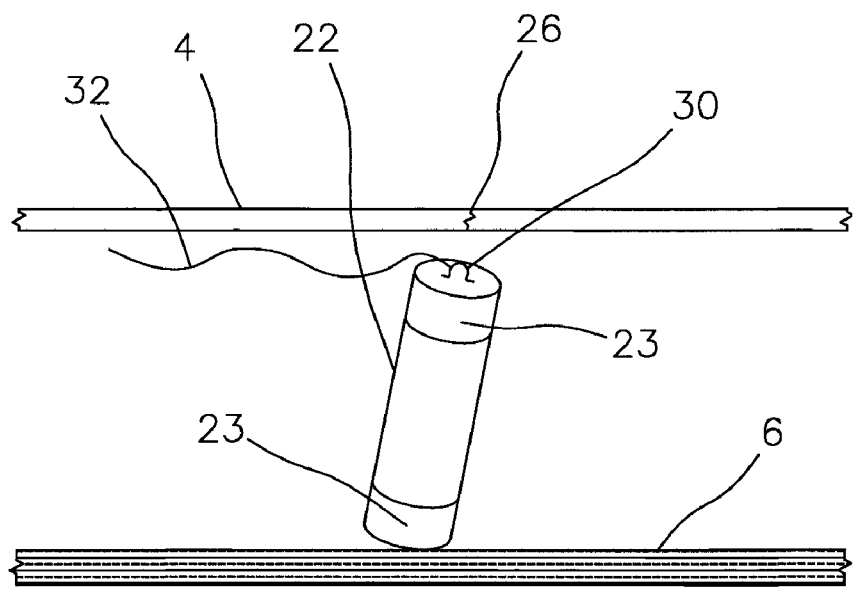
FIG. 2 depicts an implanted microstimulator at a nerve.

Once the microstimulator 22 is placed in close communication with the nerve 6, by passing the microstimulator 22 down the length of the inner sheath 8, the microstimulator 22 is activated and powered via an externally provided RF signal and the muscle that responded previously is observed to see if it is still responding when stimulated by the microstimulator 22. Alternately the microstimulator 22 may be activated by an RF signal or powered by means other than by an RF signal, such as by an internal battery. If the muscle is responding properly, the outer sheath 16 is pulled back while restraining the microstimulator 22 with the blunt-end push rod 24 (see FIG. 1). The microstimulator 22 is free of the outer sheath 16 and both the outer sheath 16 and blunt-end push rod 24 are removed from the living tissue. The microstimulator 22 remains in position next to the nerve 6 and at the base of insertion point 26, as illustrated in FIG. 2, after the outer sheath 16 and the blunt-end push rod 24 have been removed.

The microstimulator 22 (FIG. 1) contains removal loop 30, e.g., preferably an eyelet, on the end nearest the skin 4 to facilitate permanent, locking attachment of tether 32 to the microstimulator 22. The end of the tether 32, preferably a string, may be left in the living tissue near the insertion point 26 (FIG. 2) or its end may be left outside the living tissue. The tether 32 may be used to locate and/or to remove the microstimulator by pulling on it with a tensile force. This surgical technique is performed under the auspices of a surgeon and is effective for a few days post-surgery to remove the microstimulator 22 without risking further damage or trauma to the implant area, until the tissue begins to heal and adhere to the microstimulator.

Figure 3:
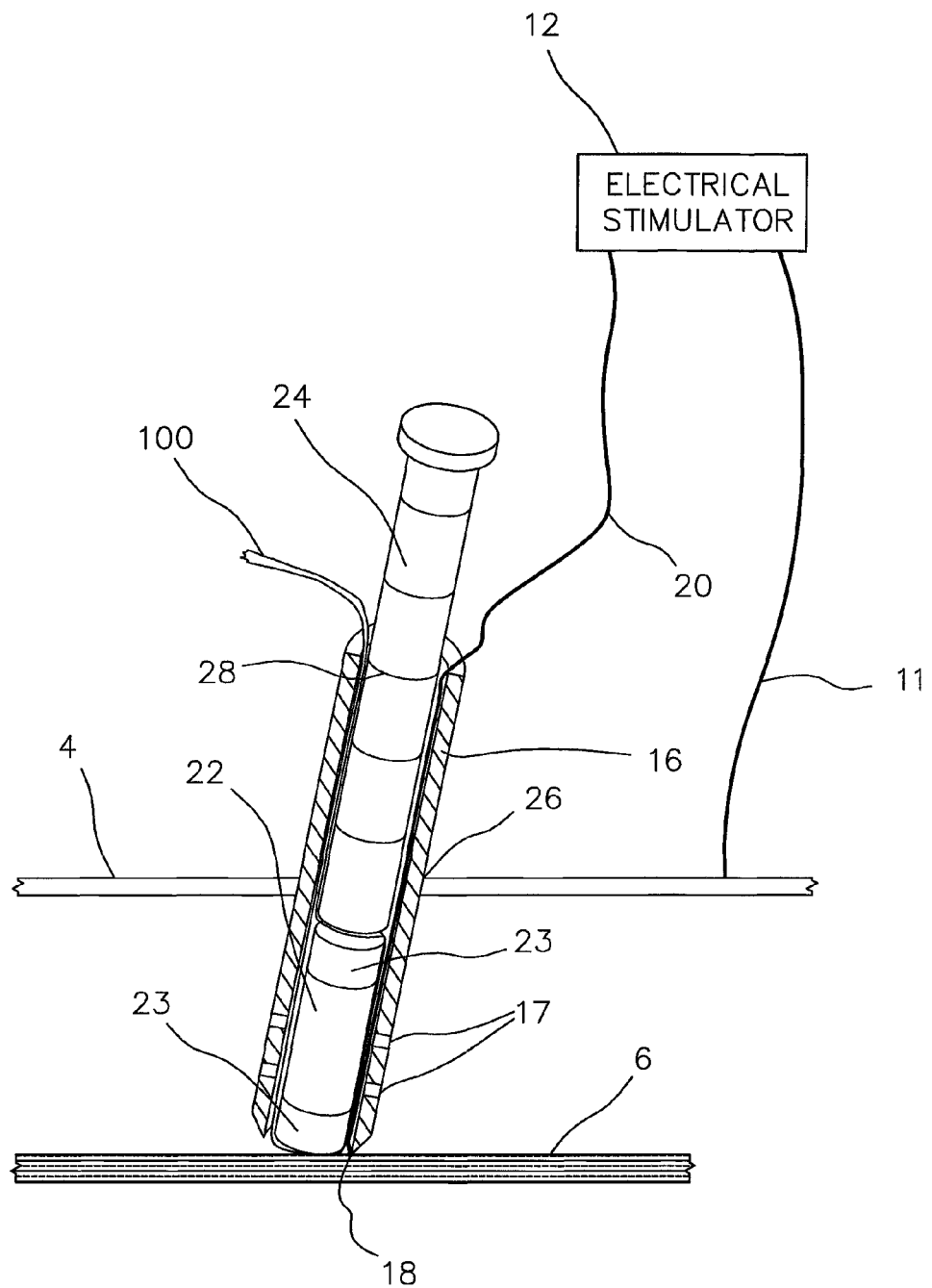
FIG. 3 illustrates an outer sheath and sheath electrode near a nerve with a microstimulator that is contained in a silk tube being inserted by a blunt-end push rod.

An alternative embodiment to the removal system using the tether 32 connected to the removal loop 30 on the microstimulator 22 (FIGS. 1 and 2) is to place the microstimulator 22 in a porous, non-soluble, biocompatible fabric tube 100 (FIG. 3). A preferred material for biocompatible fabric tube 100 is a silk tube, which is essentially a "sock" or closed end tube. Silk is a preferred material because it is biocompatible and does not bond readily to the living tissue. As an alternative to silk, any closely woven material made of non-soluble material may be used. Alternatives include dialysis membrane materials. The ideal material is porous to allow solute materials to penetrate and flood the microstimulator surfaces for optimum electrical contact, however the structure of the materials must be so fine that the body's connective tissue cannot penetrate and lock the fabric tube 100 into place. Should the microstimulator 22 need to be removed, then the end of the fabric tube 100 is located either protruding from the skin 4 or implanted beneath the skin 4 near insertion point 26, and withdrawn from the living tissue with the microstimulator 22 inside.

The following non-limiting example sets forth an exemplary surgical implantation procedure for implanting a miniature implantable stimulator or sensor, e.g., the BION® that is available from Advanced Bionics Corporation, by using an embodiment of the present invention.

MICROSTIMULATOR IMPLANTATION PROCEDURE, ANTERIOR APPROACH, FOR SLEEP APNEA

1. Instruct the patient to lie down in the supine position.
2. Prepare the patient for surgery using standard surgical preparation.
3. Anesthetize the skin and subcutaneous tissue with 1% xylocaine/1:100,000 epinephrine at and around the insertion site in the neck.
4. Anesthetize one nostril and the nasopharynx with topical lidocaine/oxymetazoline solution and insert a laryngoscope to observe tongue movement during hypoglossal nerve stimulation.
5. Mark the midpoint of the hyoid bone and mark a point about 1 cm anterior/superior to the hyoid with a sterile pen. Make an incision about 1 cm wide parallel to the hyoid extending down into the subcutaneous tissue about 5 mm mid center over the 1 cm anterior point. Use an intravenous sedative as required.
6. Attach the electrical stimulator cathodal connecting lead to the proximal end of the blunt tipped electrode probe. The electrical stimulator anode lead is attached to a surface electrode placed on the exposed shoulder.
7. Insert the probe into the incision about 5-6 mm off the midline at a right angle to the skin. Advance the probe slowly inward at about 15 degrees laterally off the perpendicular toward the hypoglossal nerve.
8. Turn the electrical stimulator on (at approximately 30 pulses/sec, 3 mA, 200 μsec) and advance the probe slowly inward toward the hypoglossal nerve (HGN) until a contraction of the tongue is observed. Increase the stimulation current to 5-10 mA for brief periods, if required, to optimally position the probe. Check with the patient to ensure comfort at this level.
9. Remove the cathodal connecting lead from the probe. Connect the sheath lead wire to the electrical stimulator. Slide the inner sheath and outer sheath near the tip of the probe by observing location marks on the probe.
10. Turn the electrical stimulator on (at approximately 30 pulses/sec, 3 mA, 200 μsec) and advance the inner sheath and the outer sheath slowly toward the optimum position near the hypoglossal nerve (HGN) until a contraction of the tongue is observed. It may be necessary to increase the stimulation current to 5-10 mA for brief periods while searching for the optimum location for the best response of the muscle. Check with the patient to ensure comfort at this level.
11. While holding the inner sheath and outer sheath, pull the probe gently out of the inner sheath. Detach the outer sheath from the inner sheath. Holding the outer sheath, withdraw the inner sheath 3-4 cm.
12. Attach a 5 ml syringe, filled with normal sterile saline (0.9% NaCl), to the inner sheath and inject a few drops into the inner sheath, then remove the inner sheath. Then, insert the microstimulator into the outer sheath. The microstimulator is positioned by pushing it with the inner sheath, which is marked on its shaft to indicate when the tip microstimulator is at the tip of the outer sheath. Add more saline into the outer sheath through the inner sheath, ensuring that the anode will make electrical connection to the tissue through the small holes in the outer sheath's wall.
13. To ensure proper microstimulator position, turn the electrical stimulator on and confirm that a contraction of the tongue is observed when it is stimulated with the sheath electrode. Then activate the microstimulator external coil and controller. If the microstimulator does not contract the genioglossus muscle (GGM) adequately, then withdraw the microstimulator while it is still in the outer sheath. Then reposition the microstimulator using the outer sheath and sheath electrode to determine the optimum position. If the response is similar to that evoked using the electrical stimulator and probe, then pull the outer sheath gently up to the second mark on the inner sheath, while holding the inner sheath and microstimulator stationary in the fixed position, so the microstimulator is extruded and placed in position. After the microstimulator is extruded, remove the outer sheath and inner sheath from the patient, and then test the microstimulator again for position near the nerve using the external coil and controller. If the microstimulator has moved after being extruded from the outer sheath (verified by stimulation and poor GGM response while the microstimulator pickup electrodes indicate good coupling), then withdraw the microstimulator along the surgically created surgical implantation path by the attached removal loop, and reintroduce using steps 10-13.

14. If the microstimulator is in the correct location and is able to stimulate the GGM satisfactorily, then the emerging removal loop is threaded onto a small curved needle and sewn to the subcutaneous tissues. Close the subcutaneous layer with dissolvable sutures and the skin with monofilament nylon sutures. Keep the skin sutures in place for approximately 10 days.

FIG. 4 provides an end view of a preferred embodiment of a removal loop 508, e.g., eyelet, having an eyelet hole 510 therethrough, where the removal loop 508 is tapered to facilitate its removal through living tissue when tether 512 (see FIG. 5) is pulled so as to urge the miniature implantable device 502, e.g., microstimulator, microsensor, or other microdevice, to be removed from the living tissue without the necessity of additional surgery. The miniature implantable microdevice 502 preferably has an axial dimension of less than 60 mm and a lateral dimension of less than 6 mm. Its volume displacement is less than about 2,000 cubic mm. Removal of the miniature implantable microdevice 502 may be accomplished by pulling on tether 512, thereby avoiding the risk of additional surgery, wherein the muscle and tissue may inadvertently be injured.

The miniature implantable microdevice 502 can be removed after an implantation for about two weeks before the surrounding tissue heals such that the device can only be removed after surgically creating a removal path for it. The tether 512 provides the ability to apply up to about 5 pounds of tensile force exerted as a pull on the device, where the device will withstand in excess of 10 pounds of pulling force without experiencing damage. This method of removal eliminates the need for special tools and greatly reduces the likelihood of damage during removal.

FIG. 5 depicts a side view of the miniature implantable microdevice, generally 502, where one end of the miniature implantable device 502 is the distal electrode end 506 and the other end is the proximal electrode end 504. Integrally attached to the proximal electrode end 504 is an eyelet 508 having a hole therethrough for receiving a tether 512 which in a preferred embodiment is a string of about 4-0 or 5-0 diameter. Eyelet 508 is preferably attached by welding to the proximal electrode end 504, although it can be equally well attached by any known method of attachment, such as soldering or brazing, to any metal or ceramic end of the miniature implantable device 502. The tether 512 is attached by tying it into a knot after passing through eyelet hole 510. The tether 512 may equally well be tied into a loop or it may be attached by any of several known methods, such as by using a fastener.

The eyelet 508 is formed from a material that facilitates the conduction of electrical signals from the electronic microdevice to the living tissue. Preferred materials are platinum, iridium, or alloys of platinum and iridium. These materials offer the advantage of providing an eyelet 508 that possesses a low metal-to-electrolyte voltage drop by virtue of improved electrical coupling to a saline solution, and/or an efficient electron-to-ion transduction factor when implanted in living tissue, compared to known electrode materials, such as titanium or titanium alloys. This translates to improved performance of the implanted miniature microdevice 502, such as increased battery life.

Tether 512 is depicted in FIG. 5 attached at one end to eyelet 508 and at the other end to a radio-opaque marker 514, which is located near the skin to facilitate its being located and removed from the living tissue to allow the miniature implantable device 502 to be removed. Alternatively, the tether may be radio-opaque string, such as by the addition of $TiO_2$ or $Al_2O_3$ to the tether, so that it may be located by X-ray, to facilitate removal of miniature implantable device 502. In a further alternative embodiment, the tether may be electrically conductive. It is preferable to have the tether electrically conductive when it is attached to the return electrode of the microstimulator to decrease the electrical resistivity of the living tissue to the return electrical circuit, thereby improving the performance of the implanted microstimulator.

FIG. 6 depicts an end view of the microstimulator 502 from the distal end showing the distal electrode end 506. The removal loop 508 at the proximal electrode end 504 is shown with dashed lines.

FIG. 7 is an end view of an alternative embodiment of an eyelet where the eyelet is a uniformly shaped nipple removal loop 516 on the end of miniature implantable device 502, with a hole passing through nipple eyelet 516 to attach to tether 512.

The side view of nipple eyelet 516 of FIG. 8 shows tether 512 attached to both the hole that passes through nipple removal loop 516 and to the radio-opaque marker 514.

An alternative embodiment of an eyelet is shown in FIGS. 9 and 10 where the removal loop is cylinder eyelet 518 having a hole therethrough for attachment to tether 512.

A further alternative embodiment is shown in FIGS. 11 and 12 where the electrode 520 has a circumferential ring 522 that is a groove around the electrode 520 rather than a through hole, as previously presented, for attachment to the tether 512. The tether 512 is preferentially attached by tying it securely around circumferential ring 522, although alternate methods of attachment are envisioned as well.

GLOSSARY

Terms are to be interpreted within the context of the specification and claims. The following terms of art are defined and shall be interpreted by these definitions. Medical terms that are not defined here shall be defined according to The American Heritage Stedman's Medical Dictionary, Houghton Mifflin, 1995, which is included by reference in its entirety. Terms that are not defined here shall be defined according to definitions from the ASM Metals Reference Book, $3^{rd}$ Edition, 1993, which is included by reference in its entirety.

Biocompatible. The ability of a long-term implantable medical device to perform its intended function, with the desired degree of incorporation in is the host, without eliciting any undesirable local or systemic effects in that host. Regulatory agencies require that implanted objects or devices within the human body be biocompatible.

Body. The entire material or physical structure of an organism, especially of a human.

Bond. In welding, brazing, or soldering, the junction of joined parts. Where filler metal is used, it is the junction of the fused metal and the heat-affected base metal.

Braze. Bonding by heating an assembly to suitable temperature and by using a filler metal having a liquidus above 450° C. (840° F.) and below the solidus of the base metal. The filler metal is distributed between the closely fitted faying surfaces of the joint by capillary action.

Butt joint. A joint between two abutting members lying approximately in the same plane.

Cavity. The hollow area within the body, such as a sinus cavity, vagina, mouth, anus, or ear.

Filler metal. Metal added in making a brazed, soldered, or welded joint.

Foil. Metal in sheet form less than 0.15 mm (0.006 inches) thick.

Hermetic. Completely sealed by fusion, soldering, brazing, etc., especially against the escape or entry of air or gas.

Implant. To embed an object or a device in a body surgically along a surgically created implantation path.

Insert. To place an object or a device into a body cavity.

Interlayer. See Foil.

Joined. Fastened together by brazing, welding, or soldering.

Liquidus. In a phase diagram, the locus of points representing the temperatures at which the various compositions in the system begin to freeze on cooling or finish melting on heating.

Microstimulator. An implantable, biocompatible device having dimensions that are less than about 6 mm diameter and 60 mm in length that is capable of sensing or stimulating electrical signals within living tissue.

Noble metal. A metal with marked resistance to chemical reaction, particularly to oxidation and to solution by inorganic acids.

Roll bonding. The same as roll welding and forge welding. A solid-state process where metals are forced together while hot by applying very high pressure that is asserted by rolls to form plate, sheet or foil material and not complex shapes. No filler material is used to achieve roll bonding.

Soldering. A group of processes that join metals by heating them to a suitable temperature below the solidus of the base metals and applying a filler metal having a liquidus not exceeding 450° C. (840° F.). Molten filler metal is distributed between the closely fitted surfaces of the joint by capillary action.

Solid-state welding. A group of processes that join metals at temperatures essentially below the melting points of the base materials, without the addition of a brazing or soldering filler metal. Pressure may or may not be applied to the joint.

Solidus. In a phase diagram, the locus of points representing the temperatures at which various compositions stop freezing upon cooling or begin to melt upon heating.

Subcutaneous. Located, found, or placed just beneath the skin.

Surgery. A procedure involving the cutting or intrusive penetration of body tissue by cutting or penetration and not by inserting an object or a device into a naturally existing body cavity.

Surgical. Of, relating to, or characteristic of surgeons or surgery.

Obviously, many modifications and variations of the present invention are possible in light of the above teachings. For example, while the aforedescribed removal structures may be used with the aforedescribed implantation structures, they are equally useful when the implanted devices, e.g., microdevices, have been implanted by cut-down techniques. Further, the term "tether" may include devices, such as, but not limited to, string, cord, thread, wire, ribbon, lace, line, gut, or suture, etc. Thus, any slender, elongated, threadlike object or structure, made by any method, is applicable to the present invention. It is therefore to be understood that, within the scope of the appended claims, the invention may be practiced otherwise than as specifically described.

What is claimed is:

1. A method for surgically implanting and removing from living tissue an implanted electronic microdevice selected from the group consisting of a sensor or a stimulator, said microdevice having an axial dimension of less than 60 mm and a lateral dimension of less than 6 mm, comprising the steps of:

selecting a biocompatible fabric tube;

placing said electronic microdevice in said biocompatible fabric tube;

surgically creating an insertion point in skin and a path for said microdevice in the living tissue;

surgically implanting said fabric tube contained microdevice in the living tissue through the insertion point in the skin along the insertion path;

determining the position of the microdevice relative to a target nerve;

removing said microdevice by pulling said biocompatible fabric tube along said insertion path toward said insertion point; and removing said microdevice from the living tissue through said insertion point.

2. The method for removal according to claim 1 wherein said step of selecting a biocompatible fabric tube comprises selecting a biocompatible tube formed from silk.

* * * * *